(12) United States Patent  (10) Patent No.: US 12,150,869 B2
Steinberg et al.  (45) Date of Patent: *Nov. 26, 2024

(54) INTERCHANGEABLE DISTAL END FOR A PROSTHETIC SOCKET SYSTEM

(71) Applicant: Ossur Iceland ehf, Reykjavik (IS)

(72) Inventors: Marco Steinberg, Reykjavik (IS); Sigurdur Hannesson, Reykjavik (IS); Andrew Bache, Reykjavik (IS)

(73) Assignee: Ossur Iceland ehf, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 18/194,770

(22) Filed: Apr. 3, 2023

(65) Prior Publication Data

US 2023/0248550 A1  Aug. 10, 2023

Related U.S. Application Data

(63) Continuation of application No. 17/462,508, filed on Aug. 31, 2021, now Pat. No. 11,642,233.
(Continued)

(51) Int. Cl.
A61F 2/78 (2006.01)
A61F 2/80 (2006.01)
(Continued)

(52) U.S. Cl.
CPC .............. *A61F 2/7812* (2013.01); *A61F 2/80* (2013.01); *A61F 2002/5007* (2013.01); *A61F 2002/5083* (2013.01); *A61F 2002/6614* (2013.01)

(58) Field of Classification Search
CPC .. A61F 2/7812; A61F 2/76; A61F 2/80; A61F 2002/5007; A61F 2002/5083; A61F 2002/785; A61F 2002/7875
See application file for complete search history.

(56) References Cited

U.S. PATENT DOCUMENTS 37,282 A  1/1863  Engelbrecht et al.
51,593 A  12/1865  Jewett
(Continued)

FOREIGN PATENT DOCUMENTS

CA  2854799 A1  5/2013
CA  2889617 A1  5/2014
(Continued)

OTHER PUBLICATIONS

Initial and Interim Prostheses [Retrieved from Internet on Feb. 11, 2013], <URL:http://www.ottobockus.com/cps/rde/xbcr/ob_us_en/08cat_4.pdf>. Published in Prosthetics Lower Extremities 2008, see contents page <URL:http://www.ottobockus.com/cps/rde/xbcr/ob_us_en/08cat_1.pdf> pp. 24-31.
(Continued)

*Primary Examiner* — Christie Bahena
(74) *Attorney, Agent, or Firm* — Workman Nydegger

(57) ABSTRACT

A prosthetic socket system having an interchangeable distal end, includes a prosthetic socket defining a substantially rigid base, and a funnel formed from a polymeric material and removably attached to the base of a prosthetic socket. The funnel is arranged to be positioned in the base, and is configured and dimensioned to accommodate a distal end of a residual limb.

12 Claims, 9 Drawing Sheets

Related U.S. Application Data

(60) Provisional application No. 63/074,948, filed on Sep. 4, 2020.

(51) Int. Cl.
  *A61F 2/50* (2006.01)
  *A61F 2/66* (2006.01)

(56) References Cited

U.S. PATENT DOCUMENTS

| | | |
|---|---|---|
| 366,494 A | 7/1887 | Marks |
| 470,431 A | 3/1892 | Marks |
| 980,457 A | 1/1911 | Toles |
| 1,066,605 A | 7/1913 | Hanger |
| 1,082,256 A | 12/1913 | Apgar |
| 1,144,681 A | 6/1915 | Apgar |
| 1,398,824 A | 11/1921 | Abrams |
| 1,861,311 A | 5/1932 | Logan |
| 1,893,853 A | 1/1933 | Tullis |
| 2,025,835 A | 12/1935 | Trautman |
| 2,229,728 A | 1/1941 | Eddels |
| 2,530,285 A | 11/1950 | Catranis |
| 2,533,404 A | 12/1950 | Sharp et al. |
| 2,634,424 A | 4/1953 | O'Gorman |
| 2,669,728 A | 2/1954 | Ritchie |
| 2,671,225 A | 3/1954 | Schoene et al. |
| 2,759,271 A | 8/1956 | Duyke |
| 2,808,593 A | 10/1957 | Andersen |
| 2,908,016 A | 10/1959 | Botko |
| 2,949,674 A | 8/1960 | Wexler |
| 3,393,407 A | 7/1968 | Kandel |
| 3,671,980 A | 6/1972 | Baird |
| 3,678,587 A | 7/1972 | Madden |
| 4,128,903 A | 12/1978 | Marsh et al. |
| 4,161,042 A | 7/1979 | Cottingham et al. |
| 4,216,550 A | 8/1980 | Thompson |
| 4,225,982 A | 10/1980 | Cochrane et al. |
| 4,268,922 A | 5/1981 | Marsh et al. |
| 4,283,800 A | 8/1981 | Wilson |
| 4,300,245 A | 11/1981 | Saunders |
| 4,459,709 A | 7/1984 | Leal et al. |
| 4,564,365 A | 1/1986 | Winer et al. |
| 4,704,129 A | 11/1987 | Massey |
| 4,715,124 A | 12/1987 | Harrington |
| 4,783,293 A | 11/1988 | Wellershaus et al. |
| 4,842,608 A | 6/1989 | Marx et al. |
| 4,872,879 A | 10/1989 | Shamp |
| 4,921,502 A | 5/1990 | Shamp |
| 4,923,474 A | 5/1990 | Klasson et al. |
| 4,938,775 A | 7/1990 | Morgan |
| 4,988,360 A | 1/1991 | Shamp |
| 5,003,969 A | 4/1991 | Azer et al. |
| 5,007,937 A | 4/1991 | Fishman et al. |
| 5,014,441 A | 5/1991 | Pratt |
| 5,108,456 A | 4/1992 | Coonan, III |
| 5,133,777 A | 7/1992 | Arbogast et al. |
| 5,139,523 A | 8/1992 | Paton et al. |
| 5,163,965 A | 11/1992 | Rasmusson et al. |
| 5,168,635 A | 12/1992 | Hoffman |
| 5,201,773 A | 4/1993 | Carideo, Jr. |
| 5,201,775 A | 4/1993 | Arbogast et al. |
| 5,226,918 A | 7/1993 | Silagy et al. |
| 5,246,464 A | 9/1993 | Sabolich |
| 5,312,669 A | 5/1994 | Bedard |
| 5,314,496 A | 5/1994 | Harris et al. |
| 5,376,129 A | 12/1994 | Faulkner et al. |
| 5,376,131 A | 12/1994 | Lenze et al. |
| 5,413,392 A | 5/1995 | Schlack et al. |
| 5,424,782 A | 6/1995 | Aoki |
| 5,503,543 A | 4/1996 | Laghi |
| 5,507,837 A | 4/1996 | Aghi |
| 5,520,529 A | 5/1996 | Heckel |
| 5,529,575 A | 6/1996 | Klotz |
| 5,529,576 A | 6/1996 | Lundt et al. |
| 5,545,231 A | 8/1996 | Houser |
| 5,549,709 A | 8/1996 | Caspers |
| 5,571,209 A | 11/1996 | Brown, Sr. |
| 5,593,454 A | 1/1997 | Helmy |
| 5,651,792 A | 7/1997 | Telikicherla |
| 5,652,053 A | 7/1997 | Liegeois |
| 5,653,766 A | 8/1997 | Naser |
| 5,658,353 A | 8/1997 | Layton |
| 5,662,715 A | 9/1997 | Slemker |
| 5,702,489 A | 12/1997 | Slemker |
| 5,718,925 A | 2/1998 | Kristinsson et al. |
| 5,724,714 A | 3/1998 | Love |
| 5,728,165 A | 3/1998 | Brown, Sr. |
| 5,728,170 A | 3/1998 | Becker et al. |
| 5,735,906 A | 4/1998 | Caspers |
| 5,779,385 A | 7/1998 | Fechter |
| 5,800,565 A | 9/1998 | Biedermann |
| 5,824,111 A | 10/1998 | Schall et al. |
| 5,882,053 A | 3/1999 | Bekins et al. |
| 5,885,509 A | 3/1999 | Kristinsson |
| 5,888,215 A | 3/1999 | Roos et al. |
| 5,888,216 A | 3/1999 | Haberman |
| 5,888,217 A | 3/1999 | Slemker |
| 5,888,234 A | 3/1999 | Littig |
| 5,867,517 A | 4/1999 | Laghi |
| 5,904,722 A | 5/1999 | Caspers |
| 5,931,872 A | 8/1999 | Lohmann |
| 5,972,036 A | 10/1999 | Kristinsson et al. |
| 6,033,440 A | 3/2000 | Schall et al. |
| 6,051,026 A | 4/2000 | Biedermann et al. |
| 6,063,125 A | 5/2000 | Arbogast et al. |
| 6,077,300 A | 6/2000 | Sabolich et al. |
| 6,106,559 A | 6/2000 | Meyer |
| 6,123,340 A | 9/2000 | Sprafka et al. |
| 6,136,039 A | 10/2000 | Kristinsson et al. |
| 6,149,691 A | 11/2000 | Fay et al. |
| 6,152,645 A | 11/2000 | Sanford |
| 6,206,932 B1 | 3/2001 | Johnson |
| 6,228,124 B1 | 5/2001 | Slemker et al. |
| 6,231,616 B1 | 5/2001 | Helmy |
| 6,231,617 B1 | 5/2001 | Fay |
| 6,231,618 B1 | 5/2001 | Schall et al. |
| 6,238,437 B1 | 5/2001 | Johnson et al. |
| 6,267,787 B1 | 7/2001 | Capper et al. |
| 6,273,918 B1 | 8/2001 | Yuhasz et al. |
| 6,287,345 B1 | 9/2001 | Slemker et al. |
| 6,334,876 B1 | 1/2002 | Perkins |
| 6,361,568 B1 | 3/2002 | Hoerner |
| 6,368,357 B1 | 4/2002 | Schon et al. |
| 6,402,789 B1 | 6/2002 | Gramnas |
| 6,406,499 B1 | 6/2002 | Kania |
| 6,440,173 B1 | 8/2002 | Meyer |
| 6,444,282 B1 | 9/2002 | Shirer |
| 6,458,163 B1 | 10/2002 | Slemker et al. |
| 6,485,776 B2 | 11/2002 | Janusson et al. |
| 6,497,028 B1 | 12/2002 | Rothschild et al. |
| 6,500,210 B1 | 12/2002 | Sabolich et al. |
| 6,508,842 B1 | 1/2003 | Caspers |
| 6,554,868 B1 | 4/2003 | Caspers |
| 6,557,177 B2 | 5/2003 | Hochmuth |
| 6,585,774 B2 | 7/2003 | Dean, Jr. et al. |
| 6,596,027 B2 | 7/2003 | Laghi |
| 6,596,028 B2 | 7/2003 | Laghi |
| 6,605,118 B2 | 8/2003 | Capper et al. |
| 6,626,951 B1 | 9/2003 | Gramnas |
| 6,645,253 B2 | 11/2003 | Caspers |
| 6,669,736 B2 | 12/2003 | Slemker et al. |
| 6,700,563 B1 | 3/2004 | Koizumi |
| 6,726,726 B2 | 4/2004 | Caspers |
| 6,761,742 B2 | 7/2004 | Caspers |
| 6,761,743 B1 | 7/2004 | Johnson |
| 6,793,682 B1 | 9/2004 | Mantelmacher |
| 6,942,703 B2 | 9/2005 | Carstens |
| 6,974,484 B2 | 12/2005 | Caspers |
| 6,991,657 B1 | 1/2006 | Price, Jr. |
| 7,056,303 B2 | 6/2006 | Dennis et al. |
| 7,090,700 B2 | 8/2006 | Curtis |
| 7,094,212 B2 | 8/2006 | Karason et al. |
| 7,097,799 B1 | 8/2006 | Burton |
| 7,105,122 B2 | 9/2006 | Karason |

(56) References Cited

U.S. PATENT DOCUMENTS

| | | |
|---|---|---|
| 7,118,602 B2 | 10/2006 | Bjarnason |
| 7,172,714 B2 | 2/2007 | Jacobson |
| 7,217,060 B2 | 5/2007 | Ingimarsson |
| 7,234,108 B1 | 6/2007 | Carstens |
| 7,240,414 B2 | 7/2007 | Taylor, Sr. |
| 7,288,116 B2 | 10/2007 | Ikeda |
| 7,300,466 B1 | 11/2007 | Martin |
| 7,318,504 B2 | 1/2008 | Vitale et al. |
| 7,338,532 B2 | 3/2008 | Haberman et al. |
| 7,344,567 B2 | 3/2008 | Slemker |
| 7,351,367 B2 | 4/2008 | Swanson, Sr. |
| 7,402,265 B2 | 7/2008 | Jacobson |
| 7,427,297 B2 | 9/2008 | Patterson et al. |
| 7,427,298 B1 | 9/2008 | Swanson, Sr. |
| 7,479,163 B2 | 1/2009 | Slemker et al. |
| 7,488,349 B2 | 2/2009 | Einarsson |
| 7,591,857 B2 | 9/2009 | Slemker et al. |
| 7,637,958 B2 | 12/2009 | Coop |
| 7,658,720 B2 | 2/2010 | Johnson, III |
| 7,727,284 B2 | 6/2010 | Warila |
| 7,753,866 B2 | 7/2010 | Jackovitch |
| 7,762,973 B2 | 7/2010 | Einarsson et al. |
| 7,771,487 B2 | 8/2010 | Mantelmacher |
| 7,867,286 B2 | 1/2011 | Einarsson |
| 7,980,921 B2 | 7/2011 | Saravanos |
| 7,985,192 B2 | 7/2011 | Sheehan et al. |
| 8,007,544 B2 | 8/2011 | Jonsson et al. |
| 8,083,807 B2 | 12/2011 | Auberger et al. |
| 8,088,320 B1 | 1/2012 | Bedard |
| 8,116,900 B2 | 2/2012 | Slemker et al. |
| 8,123,818 B2 | 2/2012 | Bjarnason et al. |
| 8,142,517 B2 | 3/2012 | Horie |
| 8,211,187 B2 | 7/2012 | Slemker et al. |
| 8,303,527 B2 | 11/2012 | Joseph |
| 8,308,815 B2 | 11/2012 | McCarthy |
| 8,323,353 B1 | 12/2012 | Alley et al. |
| 8,382,852 B2 | 2/2013 | Laghi |
| 8,403,993 B2 | 3/2013 | Aram et al. |
| 8,414,658 B2 | 4/2013 | Johnson et al. |
| 8,470,050 B2 | 6/2013 | Dillingham |
| 8,480,758 B2 | 7/2013 | McLeod |
| 8,491,667 B2 | 7/2013 | Dillingham |
| 8,535,389 B2 | 9/2013 | McKinney |
| 8,576,250 B2 | 11/2013 | Sabiston et al. |
| 8,656,918 B1 | 2/2014 | Alley et al. |
| 8,795,385 B2 | 8/2014 | Bache |
| 8,801,803 B2 | 8/2014 | Song et al. |
| 8,845,755 B2 | 9/2014 | Dillingham |
| 8,978,224 B2 | 3/2015 | Hurley et al. |
| 9,044,349 B2 | 6/2015 | Hurley et al. |
| 9,050,202 B2 | 6/2015 | Bache et al. |
| 9,198,778 B2 | 12/2015 | Celebi et al. |
| 9,248,033 B2 | 2/2016 | Bache |
| 9,283,093 B2 | 3/2016 | Alley |
| 9,468,542 B2 | 10/2016 | Hurley et al. |
| 9,468,543 B2 | 10/2016 | Hurley et al. |
| 9,474,633 B2 | 10/2016 | Williams et al. |
| 9,504,585 B2 | 11/2016 | Cornell |
| 9,549,828 B2 | 1/2017 | Hurley et al. |
| D778,452 S | 2/2017 | Cespedes et al. |
| 9,572,691 B2 | 2/2017 | Pacanowsky et al. |
| 10,172,728 B2 | 1/2019 | Hurley et al. |
| 10,179,056 B2 | 1/2019 | Hurley et al. |
| 10,206,795 B2 | 2/2019 | Pedtke et al. |
| 2001/0005798 A1 | 6/2001 | Caspers |
| 2001/0016781 A1 | 8/2001 | Caspers |
| 2002/0040248 A1 | 4/2002 | Karason |
| 2002/0087215 A1 | 7/2002 | Caspers |
| 2002/0091449 A1 | 7/2002 | Caspers et al. |
| 2002/0099450 A1 | 7/2002 | Dean, Jr. et al. |
| 2003/0144744 A1 | 7/2003 | Grubbs |
| 2003/0181990 A1 | 9/2003 | Phillips |
| 2003/0191539 A1 | 10/2003 | Caspers |
| 2004/0030410 A1 | 2/2004 | Wagman |
| 2004/0030411 A1 | 2/2004 | Caspers |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers |
| 2004/0181290 A1 | 9/2004 | Caspers |
| 2004/0236434 A1 | 11/2004 | Carstens |
| 2004/0243251 A1 | 12/2004 | Carstens |
| 2004/0260402 A1 | 12/2004 | Baldini et al. |
| 2005/0209706 A1 | 9/2005 | Warila |
| 2005/0216096 A1 | 9/2005 | Wagman |
| 2005/0244220 A1 | 11/2005 | Ingimarsson |
| 2005/0267600 A1 | 12/2005 | Haberman et al. |
| 2005/0278039 A1 | 12/2005 | Nobbe |
| 2005/0288798 A1 | 12/2005 | Curtis |
| 2006/0009860 A1 | 1/2006 | Price |
| 2006/0020348 A1 | 1/2006 | Slemker et al. |
| 2006/0135902 A1 | 6/2006 | Ingimundarson et al. |
| 2007/0004993 A1 | 1/2007 | Coppens et al. |
| 2007/0055383 A1 | 3/2007 | King |
| 2007/0078523 A1 | 4/2007 | Kholwadwala et al. |
| 2007/0152379 A1 | 7/2007 | Jacobson |
| 2007/0298075 A1 | 12/2007 | Borgia et al. |
| 2008/0066272 A1 | 3/2008 | Hammerslag et al. |
| 2008/0269914 A1 | 10/2008 | Coppens et al. |
| 2009/0036999 A1 | 2/2009 | Egilsson et al. |
| 2009/0076625 A1 | 3/2009 | Groves et al. |
| 2009/0105844 A1 | 4/2009 | Ortiz |
| 2009/0240344 A1 | 9/2009 | Colvin et al. |
| 2009/0287128 A1 | 11/2009 | Ingimundarson et al. |
| 2009/0299490 A1 | 12/2009 | Summit |
| 2010/0030344 A1 | 2/2010 | Hansen et al. |
| 2010/0036300 A1 | 2/2010 | Sheehan et al. |
| 2010/0036505 A1 | 2/2010 | Hassler |
| 2010/0082116 A1 | 4/2010 | Johnson et al. |
| 2010/0121464 A1 | 5/2010 | Mantelmacher |
| 2010/0160722 A1 | 6/2010 | Kuyava et al. |
| 2010/0191348 A1 | 7/2010 | Kettwig et al. |
| 2010/0274364 A1 | 10/2010 | Pacanowsky et al. |
| 2011/0022183 A1* | 1/2011 | Slemker .............. A61F 2/80 623/34 |
| 2011/0029096 A1 | 2/2011 | Laghi |
| 2011/0035027 A1 | 2/2011 | McCarthy |
| 2011/0071647 A1 | 3/2011 | Mahon |
| 2011/0114635 A1 | 5/2011 | Sheehan |
| 2011/0232837 A9 | 9/2011 | Ottleben |
| 2011/0307080 A1 | 12/2011 | Perkins et al. |
| 2011/0320010 A1 | 12/2011 | Vo |
| 2012/0022667 A1 | 1/2012 | Accinni et al. |
| 2012/0041567 A1 | 2/2012 | Cornell |
| 2012/0095570 A1 | 4/2012 | Marquette |
| 2012/0101417 A1 | 4/2012 | Joseph |
| 2012/0101597 A1 | 4/2012 | Bache |
| 2012/0143077 A1 | 6/2012 | Sanders et al. |
| 2012/0165956 A1 | 6/2012 | Li |
| 2012/0191218 A1 | 7/2012 | McCarthy |
| 2012/0215324 A1 | 8/2012 | King |
| 2012/0253475 A1 | 10/2012 | Kelley et al. |
| 2012/0259432 A1 | 10/2012 | Dillingham |
| 2012/0259434 A1 | 10/2012 | Dillingham |
| 2012/0271210 A1 | 10/2012 | Galea et al. |
| 2012/0271433 A1 | 10/2012 | Galea et al. |
| 2012/0283846 A1 | 11/2012 | Janssen et al. |
| 2012/0293411 A1 | 11/2012 | Leithinger et al. |
| 2012/0310371 A1 | 12/2012 | Bachus et al. |
| 2013/0123940 A1 | 5/2013 | Hurley et al. |
| 2013/0173020 A1 | 7/2013 | Slemker et al. |
| 2013/0192071 A1 | 8/2013 | Esposito et al. |
| 2013/0195540 A1 | 8/2013 | Wozencroft et al. |
| 2013/0197318 A1 | 8/2013 | Herr et al. |
| 2013/0218296 A1 | 8/2013 | Koniuk et al. |
| 2013/0245785 A1 | 9/2013 | Accini et al. |
| 2013/0282141 A1 | 10/2013 | Herr et al. |
| 2013/0282143 A1 | 10/2013 | Perkins et al. |
| 2014/0031953 A1 | 1/2014 | Mackenzie |
| 2014/0121783 A1 | 5/2014 | Alley |
| 2014/0135946 A1 | 5/2014 | Hurley et al. |
| 2014/0149082 A1 | 5/2014 | Sanders et al. |
| 2014/0227584 A1 | 9/2014 | Hurley et al. |
| 2014/0277585 A1 | 9/2014 | Kelley et al. |

(56) References Cited

U.S. PATENT DOCUMENTS

| | | | |
|---|---|---|---|
| 2015/0018974 A1* | 1/2015 | Dillingham | A61F 2/76 623/32 |
| 2015/0105867 A1 | 4/2015 | Novak | |
| 2015/0168943 A1 | 6/2015 | Hurley et al. | |
| 2015/0190252 A1 | 6/2015 | Hurley et al. | |
| 2015/0230945 A1 | 8/2015 | Bache et al. | |
| 2015/0257905 A1 | 9/2015 | Bache | |
| 2015/0265434 A1 | 9/2015 | Hurley et al. | |
| 2015/0313729 A1 | 11/2015 | Williams et al. | |
| 2015/0313730 A1 | 11/2015 | Hurley et al. | |
| 2015/0352775 A1 | 12/2015 | Geshlider et al. | |
| 2016/0000584 A1 | 1/2016 | Brown | |
| 2016/0000586 A1 | 1/2016 | Hurley et al. | |
| 2016/0000587 A1 | 1/2016 | Hurley et al. | |
| 2016/0038314 A1 | 2/2016 | Kuiken et al. | |
| 2016/0058584 A1 | 3/2016 | Cespedes et al. | |
| 2016/0120665 A1 | 5/2016 | Muller | |
| 2016/0143752 A1 | 5/2016 | Hurley et al. | |
| 2016/0158035 A1 | 6/2016 | Alley | |
| 2016/0235560 A1 | 8/2016 | Cespedes et al. | |
| 2016/0278949 A1 | 9/2016 | Dillingham | |
| 2016/0331562 A1 | 11/2016 | Bache et al. | |
| 2016/0334780 A1 | 11/2016 | Dair et al. | |
| 2016/0338858 A1 | 11/2016 | Hurley et al. | |
| 2017/0027718 A1 | 2/2017 | Williams et al. | |
| 2017/0105852 A1 | 4/2017 | Chabloz | |
| 2017/0128238 A1 | 5/2017 | Hurley et al. | |
| 2017/0143520 A1 | 5/2017 | Hurley et al. | |
| 2017/0156896 A1 | 6/2017 | Alley | |
| 2018/0000615 A1 | 1/2018 | Hurley et al. | |
| 2018/0008434 A1 | 1/2018 | Geiger et al. | |
| 2018/0020973 A1 | 1/2018 | Hurley et al. | |
| 2018/0021153 A1 | 1/2018 | Hurley et al. | |
| 2018/0153716 A1 | 6/2018 | Martin | |
| 2018/0221178 A1 | 8/2018 | Steinberg et al. | |
| 2018/0221179 A1 | 8/2018 | Bache et al. | |
| 2018/0263702 A1 | 9/2018 | Hurley et al. | |
| 2018/0296373 A1 | 10/2018 | Granz | |
| 2018/0303637 A1 | 10/2018 | Bache et al. | |
| 2018/0333279 A1* | 11/2018 | Granz | A61F 2/7812 |
| 2020/0222211 A1 | 7/2020 | Hannesson et al. | |

FOREIGN PATENT DOCUMENTS

| | | | |
|---|---|---|---|
| CN | 1793681 A | 6/2006 | |
| CN | 104884005 A | 9/2015 | |
| CN | 104053416 B | 11/2016 | |
| CN | 106913407 A | 7/2017 | |
| CN | 109328045 A | 2/2019 | |
| DE | 319623 C | 3/1920 | |
| DE | 745981 C | 5/1944 | |
| DE | 813190 C | 7/1949 | |
| DE | 1795809 U | 9/1959 | |
| DE | 2060239 A1 | 6/1972 | |
| DE | 2540138 A1 | 3/1977 | |
| DE | 2729800 A1 | 1/1979 | |
| DE | 3221920 A1 | 4/1983 | |
| DE | 3508919 A1 | 9/1986 | |
| DE | 9419208 U1 | 1/1995 | |
| DE | 19529055 A1 | 1/1997 | |
| DE | 202005018109 U1 | 3/2006 | |
| DE | 102014001000 A1 | 7/2014 | |
| EP | 0204407 A2 | 12/1986 | |
| EP | 0269391 A2 | 6/1998 | |
| EP | 1433447 A2 | 6/2004 | |
| EP | 1656911 A1 | 5/2006 | |
| EP | 2629705 A1 | 8/2013 | |
| EP | 2775967 A1 | 9/2014 | |
| EP | 2914221 A1 | 9/2015 | |
| EP | 2967925 A1 | 1/2016 | |
| EP | 2866747 B1 | 2/2017 | |
| EP | 3448323 A1 | 3/2019 | |
| EP | 3448324 A1 | 3/2019 | |
| EP | 3106134 B1 | 4/2019 | |
| GB | 127 451 A | 6/1919 | |
| GB | 267988 | 9/1925 | |
| GB | 675811 A | 7/1952 | |
| GB | 2069847 A | 9/1981 | |
| GB | 2080114 A | 2/1982 | |
| GB | 2087727 A | 6/1982 | |
| GB | 2169207 A | 7/1986 | |
| GB | 2338899 A | 1/2000 | |
| GB | 2479532 A | 10/2011 | |
| JP | 07-155343 A | 6/1995 | |
| NL | 2010991 C | 12/2014 | |
| RU | 2079292 C1 | 5/1997 | |
| RU | 2088182 C1 | 8/1997 | |
| WO | 91/16019 A1 | 10/1991 | |
| WO | 98/12994 A1 | 4/1998 | |
| WO | 0003665 A1 | 1/2000 | |
| WO | 0030572 A1 | 6/2000 | |
| WO | 0074611 A2 | 12/2000 | |
| WO | 0154631 A1 | 8/2001 | |
| WO | 03024367 A2 | 3/2003 | |
| WO | 03024370 A1 | 3/2003 | |
| WO | 03039398 A1 | 3/2003 | |
| WO | 03099173 A1 | 12/2003 | |
| WO | 2007/035875 A2 | 3/2007 | |
| WO | 2008/116025 A2 | 9/2008 | |
| WO | 2009/093020 A2 | 7/2009 | |
| WO | 2012/021823 A1 | 2/2012 | |
| WO | 2012054700 A1 | 4/2012 | |
| WO | 2013/071308 A1 | 5/2013 | |
| WO | 2014004709 A1 | 1/2014 | |
| WO | 2014005071 A1 | 1/2014 | |
| WO | 2014068269 A1 | 5/2014 | |
| WO | 2014070666 A1 | 5/2014 | |
| WO | 2014153244 A1 | 9/2014 | |
| WO | WO-2014132029 A2 * | 9/2014 | A61F 2/78 |
| WO | 2014205403 A1 | 12/2014 | |
| WO | 2015095232 A1 | 6/2015 | |
| WO | 2015143249 A1 | 9/2015 | |
| WO | 2016183065 A1 | 11/2016 | |
| WO | 2017186901 A1 | 11/2017 | |
| WO | 2017186902 A1 | 11/2017 | |
| WO | 2017194479 A1 | 11/2017 | |
| WO | 2018017959 A1 | 1/2018 | |

OTHER PUBLICATIONS

Manual: "Socket Evaluation System with the Rapid Adjustment Pylon", [retrieved from the internet on May 22, 2014], URL:http://www.fillauer.com>; 4 pages.

International Search Report from PCT Application No. PCT/US2018/033633, Nov. 22, 2018.

Alley, "The High-Fidelity Interface: Skeletal Stabilization Through Alternating Soft Tissue Compression and Release" Proceedings of the 2011 MyoElectric Controls/Powered Prosthetics Symposium Frederiction, New Brunswick, Canada, Aug. 2011. 3 Pages.

Andrysek, "Lower-Limb Prosthetic Technologies in the Developing World: A Review of Literature from 1994-2010", Prosthetics and Orthotics International, Cardiff, Wales, UK; vol. 34, No. 4, Dec. 2010; pp. 378-398.

Conn, "Materials Science: A Look at Some of the Substances on the Market for Device Fabrication", O&P Almanac, Jun. 2012, pp. 28-31; http://wwww.allardusa.com/pdf/articles/Materials%20Science%20Article%20-%20June%202012%20O%26P%20Almanac.pdf.

Fairley, M. "From Academia to the Developing World: Student Engineers Create Collaborative Technologies", The D&P Edge Magazine, OandP.com, Mar. 2011, pp. 1-9. Downloaded from http://www.oandp.com/articles/2011-05-03.asp.

Fairley, M. "M.A.S. Socket: A Transfemoral Revolution", The O&P Edge, Jun. 2004, www.oandp.com/articles/2004-06_03.asp. 5 Pages.

"COMFIL—Thermo Formable Composite Technique", Fillaur LLC and Centri, Fabrication Manuel, Jun. 15, 2012, pp. 1-13.

Gard, S.A. "Overview of Lower Limb Prosthetics Research", WRAMC and the VA Orthopedic & Prosthetic Workshop Arlington, VA, Nov., 17-18, 2003, pp. 1-49.

Geil, M.D., "Consistency, Precision, and Accuracy of Optical and Electromagnetic Shape-Capturing Systems for Digital Measure-

(56) References Cited

OTHER PUBLICATIONS ment of Residual-limb Anthropometrics of Persons With Transtibial Amputation", Journal of Rehabilitation Research and Development, vol. 44, No. 4, 2007; pp. 515-524.
Gleave, "A Plastic Socket and Stump Casting Technique for Above-Knee Prostheses", Orthopaedic and Prosthetic Appliance Department, Hong Kong Government Medical Department, The Journal of Bone and Joint Surgery, vol. 47B, No. 1, Feb. 1965, pp. 100-103.
Gerschutz, et al., "Mechanical Evaluation of Direct Manufactured Prosthetic Sockets", American Academy of Orthotists & Prosthetists, 38th Academy Annual Meeting and Scientific Symposium, U.S.A., Mar. 21-24, 2012; downloaded from http://www.oandp.org/publications/jop/2012/2012-19.pdf. 1 page.
Greenwald, et al., "vol. Management: Smart Variable Geometry Socket (SVGS) Technology for Lower-Limb Prostheses", American Academy of Orthotists & Prosthetists, vol. 15, No. 3, 2003, pp. 107-112.
Hong, et al., "Dynamic Moisture Vapor Transfer through Textiles: Part I: Clothing Hygrometry and the Influence of Fiber Type", Textile Research Journal, Thousand Oaks, California, U.S.A., Dec. 1988; 58: 697-706, Abstract. 1 Page.
Hwang, "Blooming Winner—Spark!", Spark Galleries, 2012/Spark/Concept, Spark Design Awards, 2012 3 Pages. Downloaded from http://www.sparkawards.com/galleriew/index.cfm?entry=9525D900-E0EF-59BD-46597D99 . . . .
Jana, "Designing a Cheaper, Simpler Prosthetic Arm", ZDNet, Nov. 14, 2011, pp. 1-5. Downloaded from http://www.2dnet.com/article/designing-a-cheaper-simpler-prosthetic-arm/.
Koike, et al., "The TC Double Socket Above-knee Prosthesis", Prosthetics and Orthotics International, vol. 5, 1981 pp. 129-134.
Krouskop, et al., "Computer-aided design of a prosthetic socket for an above-knee amputee", Journal of Rehabilitation Research and Development, vol. 24, No. 2 1987, pp. 31-38.
Manucharian, "An Investigation of Comfort Level Trend Differences Between the Hands-On Patellar Tendon Bearing and Hands-Off Hydrocast Transtibial Prosthetic Sockets", JPO: American academy of Orthotists & Prosthetists, Washington, D.C., U.S.A., vol. 23, No. 3, 2011: pp. 124-140.
Otto Bock Healthcare LLP, "Initial and Interim Prostheses", Otto Bock Healthcare LLP, Prosthetics Lower Extremities 2008, Feb. 2013 pp. 1-8, www.ottobockus.com/cps/rde/xbcr/ob_us_en/08cat_I.pdf.
Otto Bock Healthcare LLP , "Ottobock: PU Resin Kit Polytol"; Downloaded Dec. 17, 2012 from http://www.ottobock.com/cps/rde/xchg/ob_com_en/hs.xs1/17414.html.
Sanders, et al., "Residual limb volume change: Systematic review of measurement and management", Journal of Rehabilitation Research & Development, 2011, vol. 48, No. 8, pp. 949-986.
Sathishkumar, et al., "A cost-effective, adjustable, femoral socket, temporary prosthesis for immediate rehabilitation of above-knee amputation", International Journal of Rehabilitation Research, Ljubljana, Slovenia, Mar. 2004, vol. 27, No. 1; pp. 71-74.
SBIR topic summary: "Pro-Active Dynamic Accommodating Socket", http://www.dodsbir.net/sitis/archieves_display_topic.asp?Bookmark=34570; downloaded Mar. 25, 2013, U.S. A. 3 pages.
Smith, "Silver Linings for O&P Devices", The Academy Today, vol. 1, No. 4: Oct. 2005, 4 Pages, Downloaded from, http://www.oandp.org/AcademyTODAY/20050ct/7.asp.

Spaeth, JP , "Laser Imaging and Computer-Aided Design and Computer-Aided Manufacture in Prosthetics and Orthotics", Physical Medicine and Rehabilitation Clinics of North America, Elsevier Publishing, Amsterdam, The Netherlands; Feb. 2006 pp. 245-263, Abstract. 2 pages.
Turner, "Fit for Everyone", Yanko Design-Form Beyond Junction, Jul. 17, 2015, pp. 1-10. Downloaded from http://www.yankodesign.com/2013/07/17/fit-for-erveryone/.
"Hanger ComfortFlex Socket System for Prosthetic Devices:" Downloaded Nov. 28, 2012 from http://www.hanger.com/prosthetics/services/Technology/Pages/ComfortFlex.asp pp. 1-2.
Wilson Jr. "A Material for Direct Forming of Prosthetic Sockets", Artificial Limbs., vol. 4, No. 1, 1970, Downloaded from http://www.oandplibrary.org/al/1970_01_053.asp; downloaded Dec. 14, 2012. pp. 53-56.
Wilson, "Recent Advances in Above-Knee Prosthetics", Artificial Limbs, vol. 12, No. 2, 1968 pp. 1-27.
Wu, et al., "CIR sand casting system for trans-tibial socket", Prosthetics and Orthotics International, Aug. 2003: vol. 27, pp. 146-152.
Quigley, Michael, "Prosthetic Management: Overview, Methods and Materials," Chapter 4, Atlas of Limb Prosthetics: Surgical, Prosthetic, and Rehabilitation Principles, Second Edition, 1992, 10 Pages. Downloaded from: http://www.oandplibrary.org/alp/chapot-01.asp.
Burgess, et al. "Immediate Post-Surgical Prosthetic Fitting", The Management of Lower-Extremity Amputations, Aug. 1969, pp. 42-51.
Compton, et al., "New Plastics for Forming Directly on the Patient", Prosthetics and Orthotics International, 1978, vol. 2, No. 1, pp. 43-47, Abstract. 3 Pages.
Fairley, "Socket Can Be Fabricated, Modified, Fitted—In One Hour", The O&P Edge, Jun. 2007. 5 Pages.
"Cut-4-Custom: Custom TLSO in Less Than an Hour", The O&P Edge, Oct. 2010. 2 Pages.
"Remoldable Prosthetics", InstaMorph Moldable Plastic, http:/instamorph.com/wp-content/uploads/legcast1.png, Retrieved, May 10, 2016. 3 Pages.
International Search Report from PCT Application No. PCT/US2019/036267, Sep. 30, 2019.
International Search Report from PCT Application No. PCT/US2018/058625, Feb. 11, 2019.
English Translation of Chinese Office Action, Chinese Patent Application No. 201480010447.5, dated Mar. 3, 2016.
Pnd Office Action (and English Translation) of Chinese Patent Application No. 201480010447.5, dated Aug. 26, 2016.
Ossur, Icelock clutch 4H 214 L-214000, Instructions for Use, 3 pages.
Ossur, Icelock(r) 200 Series, Product Information, Mar. 1, 2004, 2 pages, http://www.ossur.com/print.asp?PageID=147&Redirect=False&search_string=&newsid=. . . .
Ossur, Socket Adapters, Product Information, Mar. 1, 2004, 5 pages, http://www.ossur/com/print.asp?PageID=189&Redirect=False&search_string=&newsid =. . . .
Ossur "Icelock 211 Lamination Procedure—EB345/1 JG," Technical Manual, Mar. 2003, 18 pages.
Metric Roller Clutches, https://www.sdp-si.com/ss/pdf/sscr7002.pdf.

* cited by examiner

INTERCHANGEABLE DISTAL END FOR A PROSTHETIC SOCKET SYSTEM

CROSS-REFERENCE TO RELATED APPLICATIONS

This application is a continuation of U.S. patent application Ser. No. 17/462,508, filed Aug. 31, 2021, which claims benefit of U.S. Provisional Application No. 63/074,948, filed Sep. 4, 2020. This application also relates to U.S. Patent Application Publications 2018/0303637, published Oct. 25, 2018, 2018/0333279, published Nov. 22, 2018, and 2020/0222211, published Jul. 16, 2020. Each of these patent application publications is incorporated by reference.

FIELD OF THE DISCLOSURE

The disclosure relates to interchangeable distal ends for a prosthetic socket system.

BACKGROUND

A typical prosthetic leg and foot include a socket, pylon, and foot. A socket is commonly referred to as the portion of a prosthesis that fits around and envelops a residual limb or stump, and to which prosthetic components, such as a foot, are attached. The socket's fitting and alignment are difficult tasks to perform and require extensive knowledge, training, and skill for the prosthetist.

The socket must fit closely to the stump to provide a firm connection and support but must also be sufficiently loose to allow for circulation. In combination with proper fitting, the socket must transfer loads from the residual limb to the ground comfortably.

Conventional sockets are rigid and generally have a generally uniform shape, which receives a large portion of the residual limb. These sockets are permanently formed to a static customized shape, meaning the socket does not account for shape and volume fluctuations of the residual limb. When there are shape and volume fluctuations, the fitting of the socket is impeded, with these sockets causing discomfort, pain, and soft tissue breakdown of the stump. Conventional sockets also are bulky and cumbersome to wear and may be difficult to don, making the residual limb uncomfortable when worn.

Some attempts have been made to develop adjustable sockets with individual components that can be varied in size and/or shape to account for volume and shape fluctuations of the residual limb. However, these adjustable sockets tend to have labor-intensive and complicated tightening systems for donning and doffing the socket, making their use difficult for patients with limited dexterity, cognition, and/or strength. The drawbacks can cause the unsafe and improper use of the socket, causing discomfort and even injury.

Proper fitting of the distal end of a residual limb to the socket leads to better securing of the socket to the residual limb; however, because residual limbs have varying sizes and shapes, it can be challenging to provide a universal fit.

Given the foregoing, there is a need for an adjustable socket system that overcomes the problems of existing sockets.

SUMMARY

Embodiments of the disclosure comprise an interchangeable distal end of adjustable sockets or universally fitting sockets. The interchangeable distal end is adapted to fit a variety of residual limb anatomies and may be easily adapted from the socket according to the demands incurred by the residual limb anatomies. Such demands may include sizing, shapes, fitting, and comfort.

As defined by this disclosure, the interchangeable distal ends generally refer to the combination of the socket and a funnel or insert placeable within a cavity of a prosthetic socket and located at the interior distal end. The funnel is adapted with a generally conical or partial conical shape or another suitable shape, approximating a general configuration or shape of a corresponding distal end.

The funnel intends to provide or embrace a set of differently shaped funnels configured to receive a distal end of a residual limb. The funnels may fill in voids within a distal end of the socket cavity and provide a more intimate fit between the socket and the residual limb. This arrangement is particularly beneficial when the socket is of the adjustable type that is adaptable in size according to an individual residual limb's specific sizing and shape. However, such funnels may be adapted to fit within a custom-formed prosthetic socket in the event the residual limb, particularly at the distal end, undergoes dimensional changes, and greater stability is required within the socket by which the funnel may be used and installed to take up space and provide a more intimate fit between the socket and the residual limb.

The funnel may include mounting means by which the funnel can be easily removed from the socket and swapped with another funnel better adapted to an individually shaped residual limb. The mounting means may be provided to offer more secure mounting or simplified mounting, such that the user may have ready means to change the funnels without the aid of a clinician. On the contrary, the mounting means may be sufficiently robust to require only a clinician to replace the funnel.

The funnel may be offered in various shapes, sizes, and properties to accommodate an individual user of a socket better. Such variations of the funnel may include its height relative to a mounting location of the socket, such as the extent by which it extends proximally from a distal end of the socket. Another variation may be a maximum diameter by which the funnel radially extends toward sidewalls or struts of the socket. Another variation may be the shape of the funnel, which may be configured to more intimately fit the shape of the socket or the shape of the residual limb. Yet another variation may be the material composition of the funnel, such as having softer or more rigid material properties to accommodate more sensitive areas of a residual limb. Further, another variation may be additional properties possessed by the funnel, such as being constructed from different materials at strategic locations to offer enhanced beneficial properties.

BRIEF DESCRIPTION OF THE DRAWINGS

These and other features, aspects, and advantages of the present disclosure will better understand the following description, appended claims, and accompanying drawings.

DETAILED DESCRIPTION OF VARIOUS EMBODIMENTS

Figure 1:
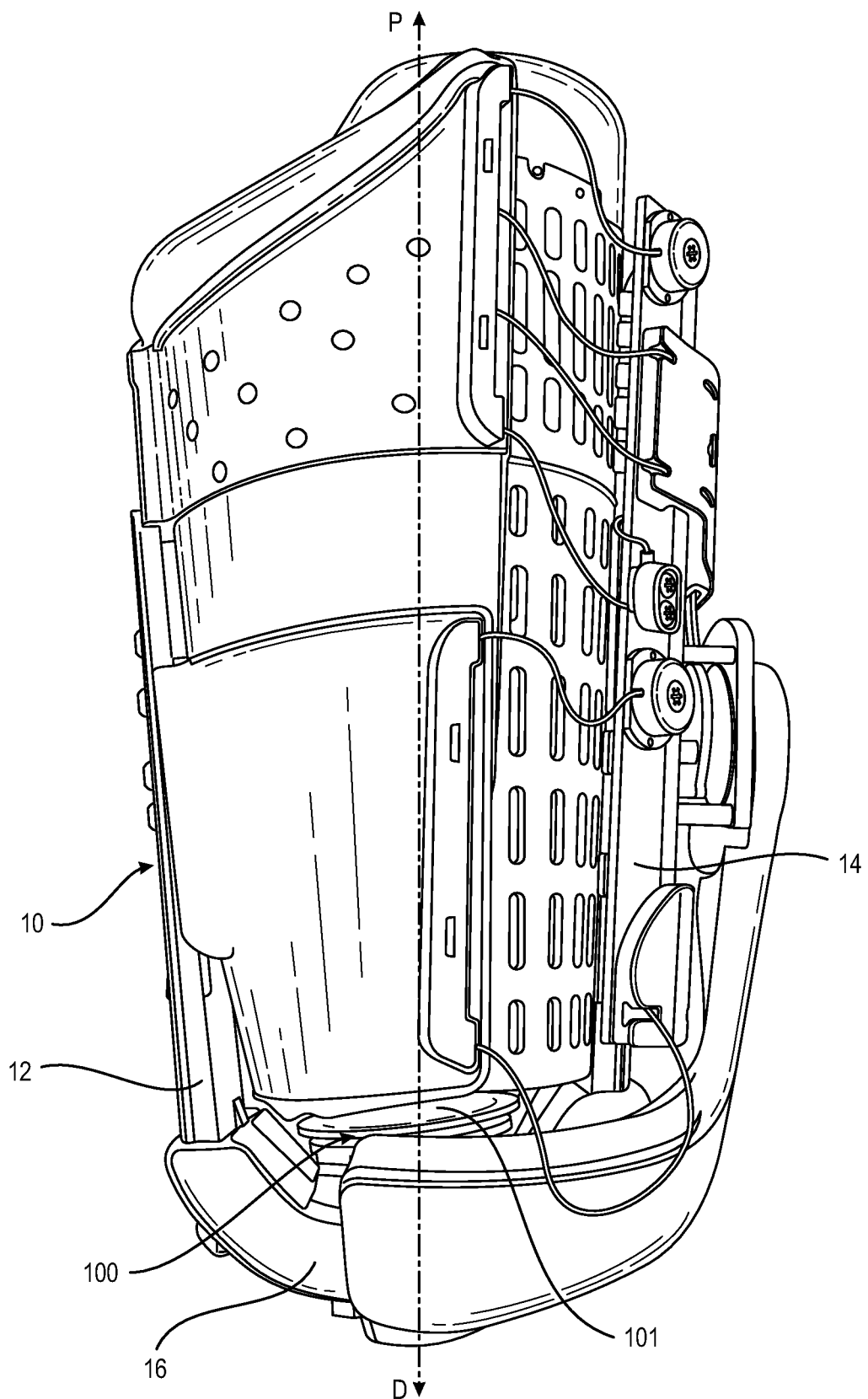
FIG. 1 is an elevational view of an adjustable socket showing proximal and distal ends and relative directions of the adjustable socket.
Figure 2A:
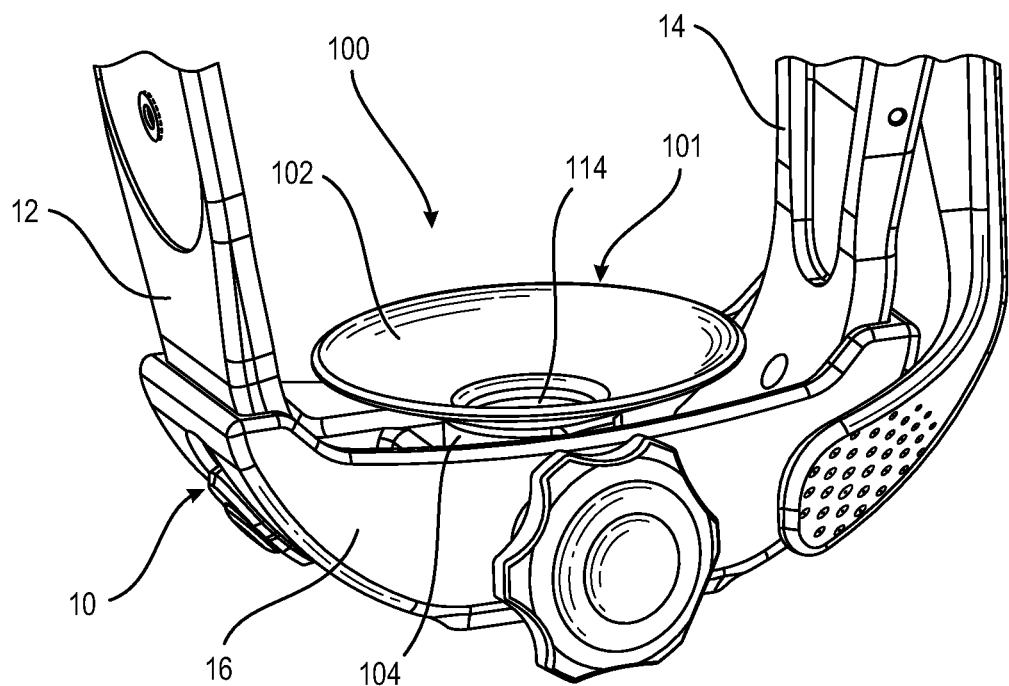
FIG. 2A is a first perspective view showing an interchangeable distal end as a funnel in a simplified view of the adjustable socket of FIG. 1.
Figure 2B:
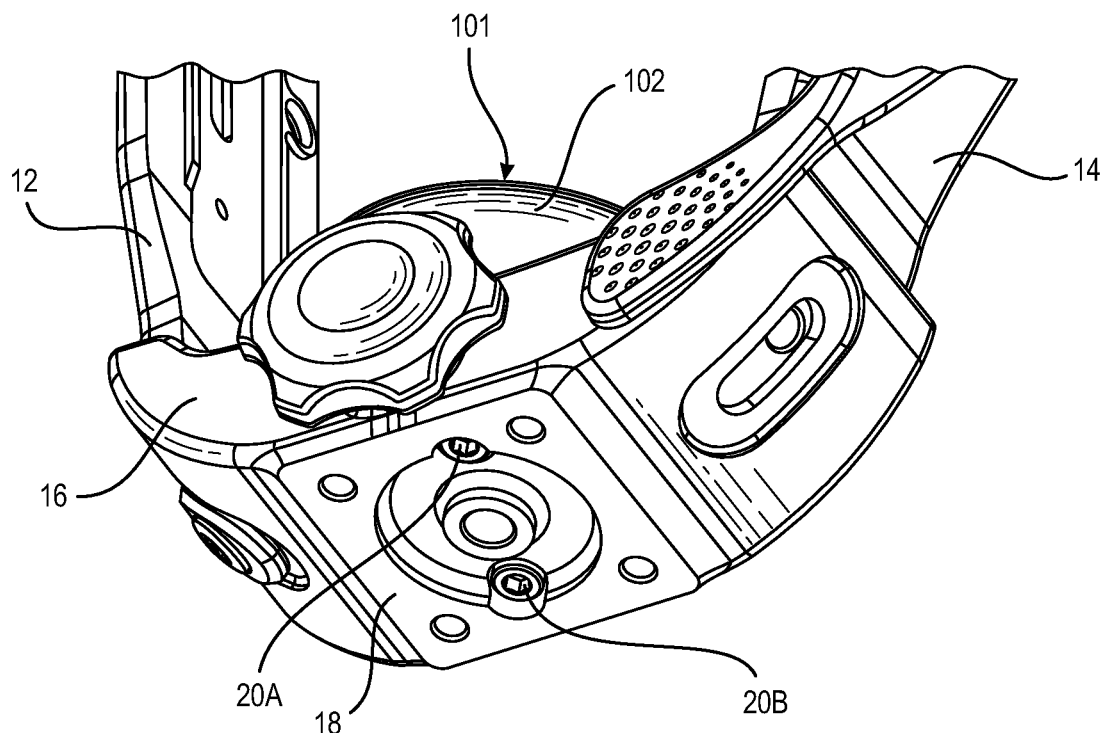
FIG. 2B is another perspective view of the funnel in the adjustable socket of FIG. 1.
Figure 2C:
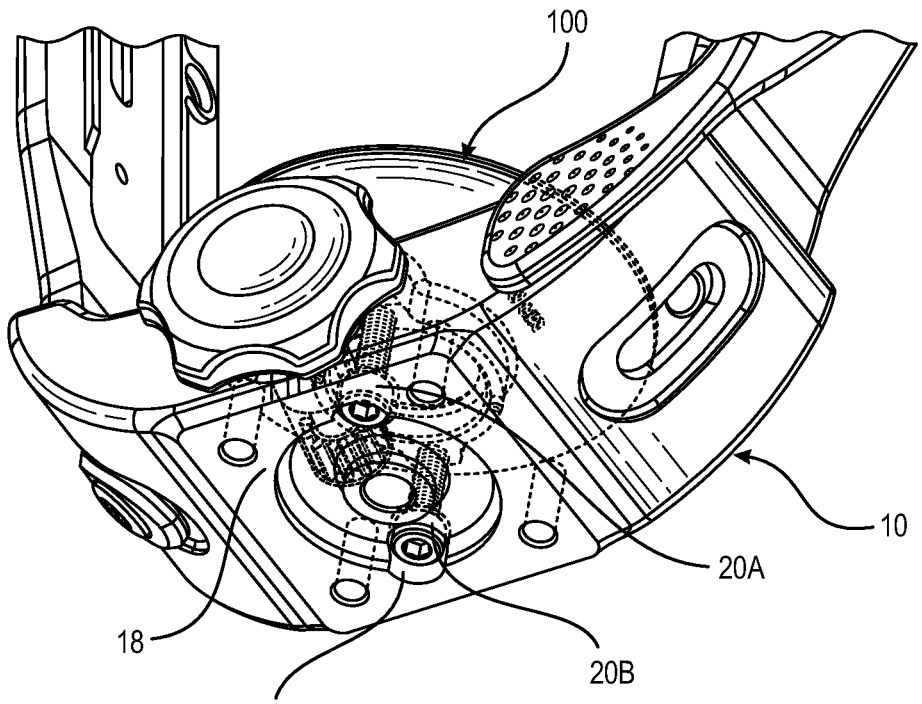
FIG. 2C is a variation of the perspective view of the funnel in FIG. 2B, showing means for mounting the funnel to the base of the adjustable socket.
Figure 2D:
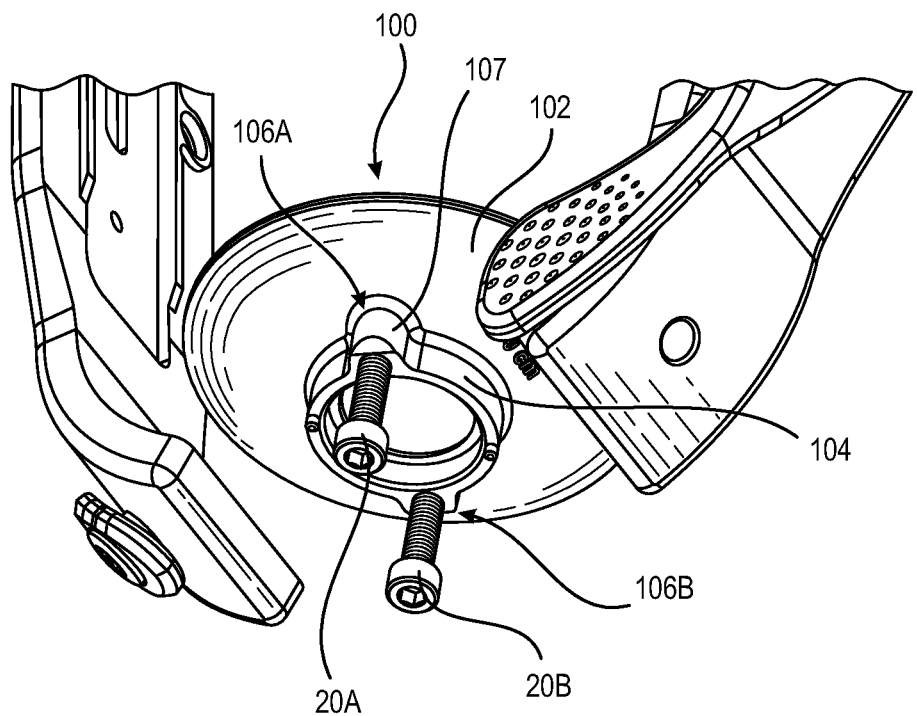
FIG. 2D is a variation of FIG. 2C with the base removed to show the means for mounting the funnel to the adjustable socket.

A better understanding of different embodiments of the disclosure may be had from the following description read with the accompanying drawings in which reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning.

Any element in a claim that does not explicitly state "means for" performing a specified function or "step for" performing a specific function is not to be interpreted as a "means" or "step" clause as specified in 35 U.S.C. section 112(f).

FIG. 1 displays an exemplary socket system 10 adapted to have an interchangeable distal end 100 according to embodiments of the disclosure. The socket system is disclosed in U.S. patent application publication 2018/0303637 and in U.S. patent application publications 2018/0333279 and 2020/0222211. However, the interchangeable distal end can likewise be provided in a conventional custom-made prosthetic socket. The interchangeable distal end comprises both components of the socket system and a removable funnel or set of funnels for attachment to a distal end D of the socket opposite a proximal end of the socket, and residing within a distal end of an internal cavity of the prosthetic socket.

According to the exemplary socket system in FIGS. 1-3B, the interchangeable distal end 100 includes a funnel 101 removably attached to a base 16 of a prosthetic socket. The funnel 101 is positionable between first and second struts 12, 14 extend from the base 16. The funnel 101 forms a stem 104 extending from the receiving portion 102. In addition, the funnel 101 forms a central opening 114 extending through the receiving portion 102 and the stem 104, and is defined along an axis A-A of the funnel 101.

The base 16 defines a distal portion 18 and has mounting means for securing the base 16 to the stem 104 of the funnel 101. The mounting means 20, 22 comprises at least one threaded hole 22 for permitting insertion and retention of fasteners 20A, 20B adapted to engage the funnel 101.

The stem 104 of the funnel 101 may form at least one mounting portion 104A, 104B. The at least one mounting portion 106A, 106B is arranged to receive the at least one fastener 20A, 20B. The at least one mounting portion 106A, 106B forms a rib 107 protruding radially from the stem 104 and generally along the length of the stem 104. The rib 107 preferably defines an opening 116A, 116B, and a threaded periphery of the opening 116A, 116B is arranged to engage the at least one fastener 20A, 20B.

The receiving portion 102 of the funnel 101 defines a receiving surface 110 adapted to receive a distal end of a residual limb. A periphery 124 of the receiving portion 102 is generally circular. As shown, the receiving surface 110 is generally conical and concave to receive a distal end of a residual limb.

More generally, the receiving surface and the receiving portion may be arranged in any shape adapted to receive a distal end of a residual limb. For example, in FIG. 3A, the periphery 108 of the receiving portion 102 has a circular portion 109 and a linear portion 111. The linear portion 111 generally corresponds to the shape of the socket while offering a sufficient surface area to receive the residual limb.

Figure 3A:
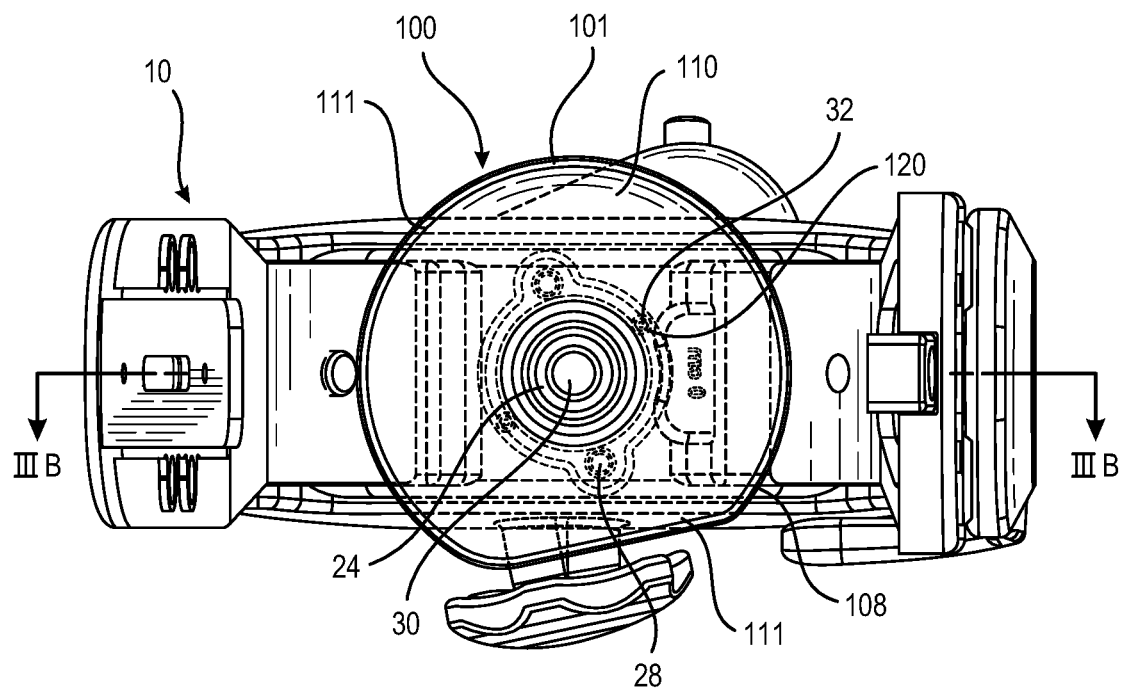
FIG. 3A is a top view of a variation of the funnel attached to the base of the adjustable socket.
Figure 3B:
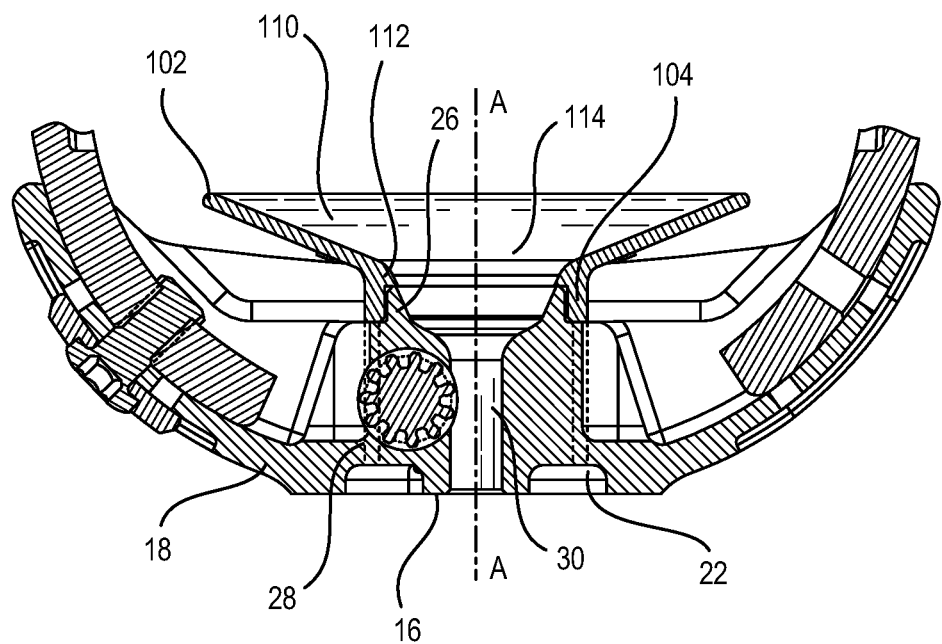
FIG. 3B is a sectional view taken along line IIIB-IIIB in FIG. 3A.

Referring to FIG. 3B, the stem 104 defines an inner notch 112 formed about the opening 114. The inner notch 112 is adapted to rest along an edge of an inner ring 26 protruding from a proximal side of the base 16 about the central opening 114. The base 16 defines an elongate opening 30 corresponding to the axis A-A of the central opening 114. The elongate opening 30 preferably permitting insertion of a locking pin, as described in U.S. 2020/0222211, therethrough. In addition, the base 16 defines elongate openings 28 adapted to correspond to the at least one threaded hole 116A, 116B of the at funnel 101.

Figure 4:
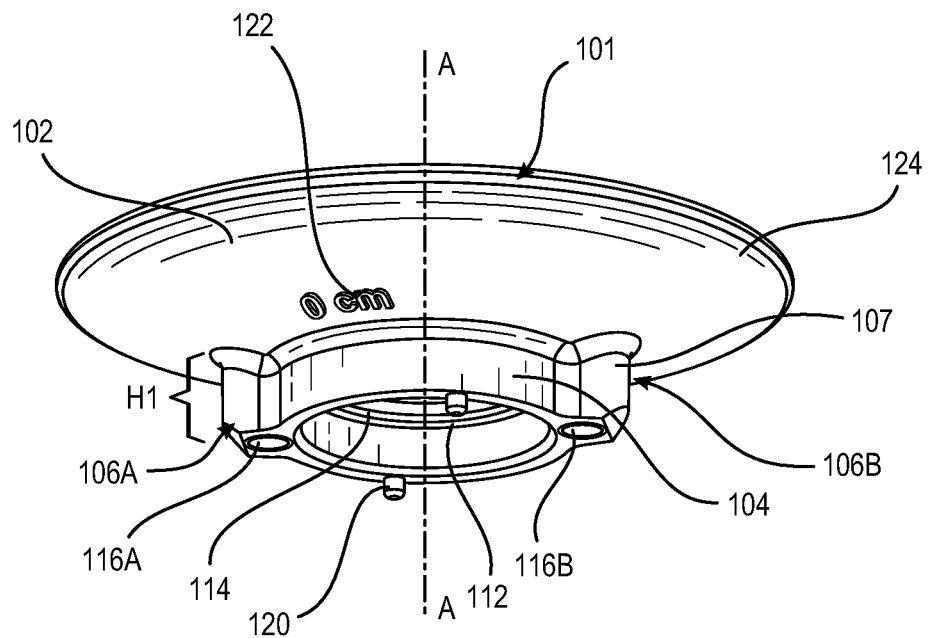
FIG. 4 is a perspective view of the funnel in FIG. 2A.

As best understood from FIGS. 3A and 4, the base 16 may define at least one aperture 32 along a proximal side of the base 16. The at least one aperture 32 is arranged to receive a protrusion 120 extending from a distal side of the funnel 101. This arrangement offers additional securing of the funnel to the base and rotational control relative to the base.

FIG. 4 shows a detailed view of the funnel 101. The funnel had a central axis A-A, and the central opening 114 extends through the central axis A-A. The receiving portion 102 is located about the central axis A-A and along a proximal portion of the funnel 101. The stem 104 extends distally from the receiving portion 102 and about the central axis A-A. As noted above, the receiving portion 102 has a generally conical shape and is concave in the distal direction to receive a distal end of a residual limb.

As in any of the disclosure embodiments, the funnel 101 preferably is formed from a polymeric material, such as an elastomer, to provide flexibility and toughness. Alternatively, the funnel 101 may be formed from a rigid polymeric material. The funnel 101 may include indicia 122 is provided on the funnel to show the height or size of the funnel 101.

Figure 5:
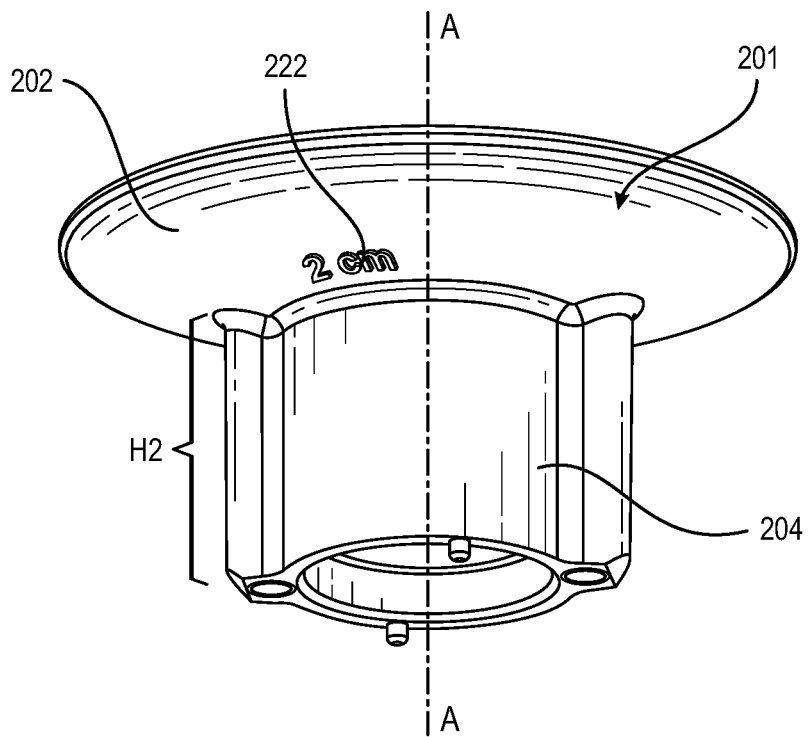
FIG. 5 is a perspective view of a variation of the funnel in FIG. 4.

Between FIGS. 4 and 5, a set of funnels may comprise the first funnel 101 having a stem 102 defining a first height H1, and a second funnel 201 having a stem 204 defining a second height H2. The first height H1 may differ from the second height H2. The different funnels may be distinguished based on other properties: height, diameter or shape of periphery of the receiving portion, or different material properties such as flexibility, compressibility, or rigidity.

Figure 6A:
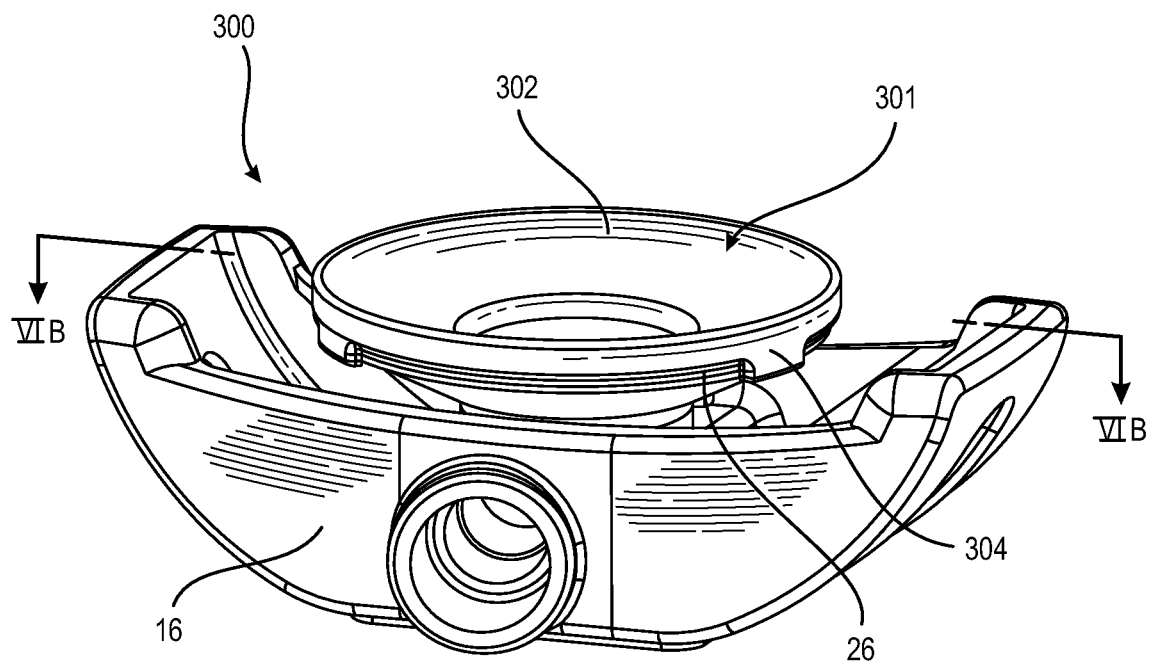
FIG. 6A is a perspective view of another embodiment of a funnel mounted in the base of FIG. 1.
Figure 6B:
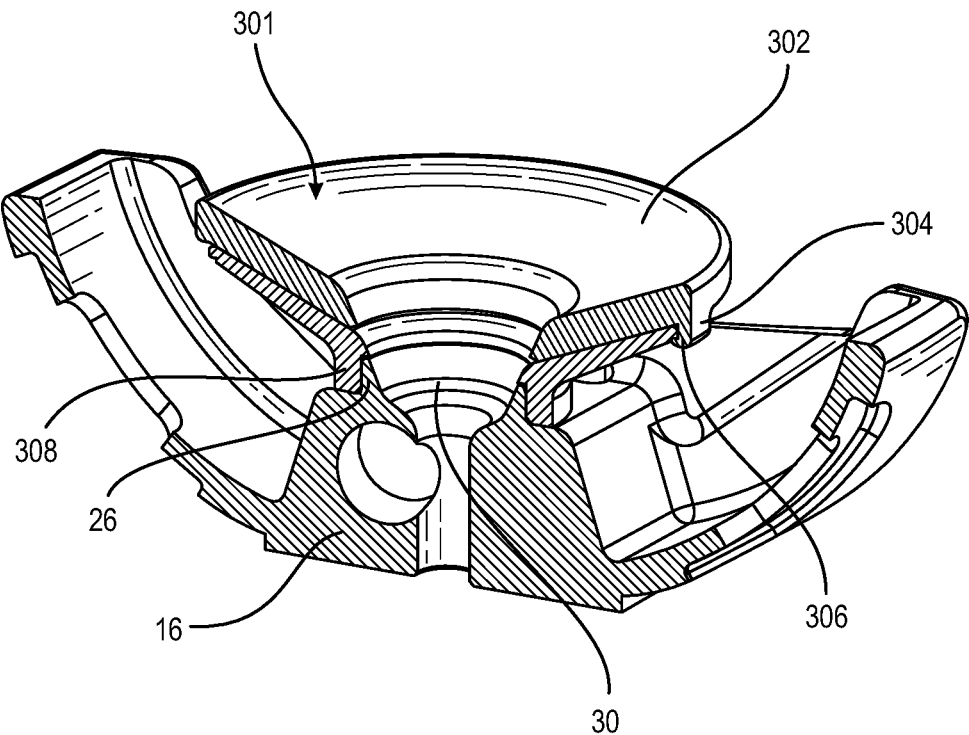
FIG. 6B is a sectional view taken along line VIA-VIA in FIG. 6A.

Referring to FIGS. 6A and 6B, another embodiment of an interchangeable distal end 300 includes a funnel 301 including a receiving portion 302 defining at least one tab 304 generally protruding axially from the receiving portion 302 and being adapted to secure to an annular insert 308 formed to attach to the base 16. The at least one tab 304 defines a hook 306 engageable with an edge of the annular insert 308. The funnel 301 may be formed from a resilient material, and the at least one tab 304 may be adapted to resiliently secure to the annular insert 308. In addition, the annular insert 308 may be adapted to secure to the inner ring 26.

Figure 7A:
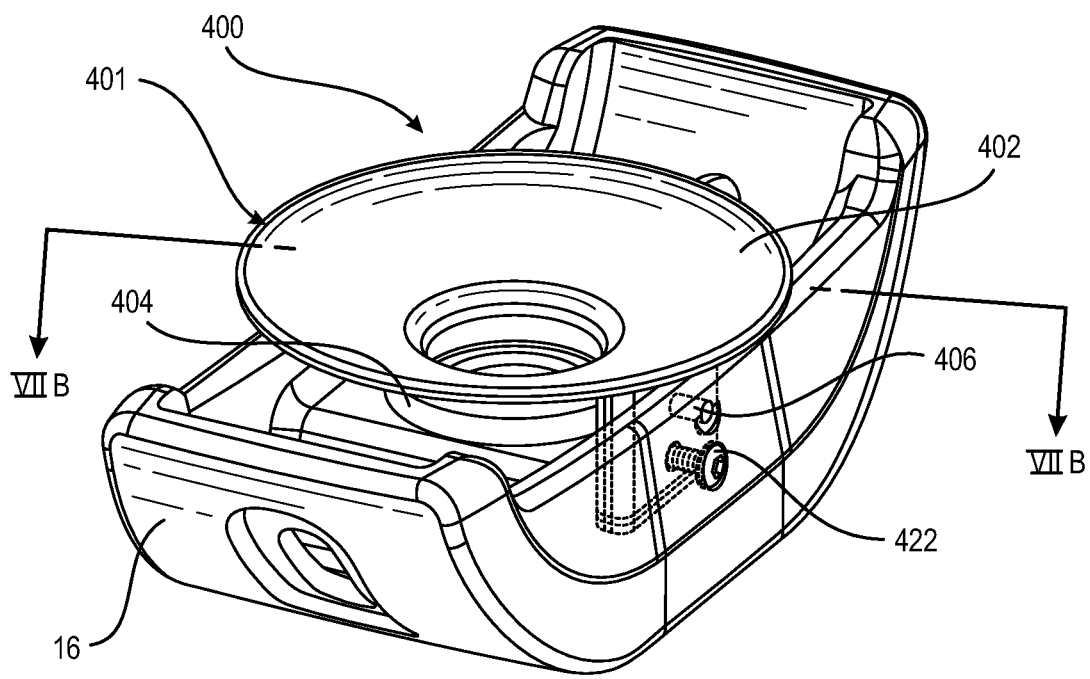
FIG. 7A is a perspective view of another embodiment of a funnel mounted in the base of FIG. 1.
Figure 7B:
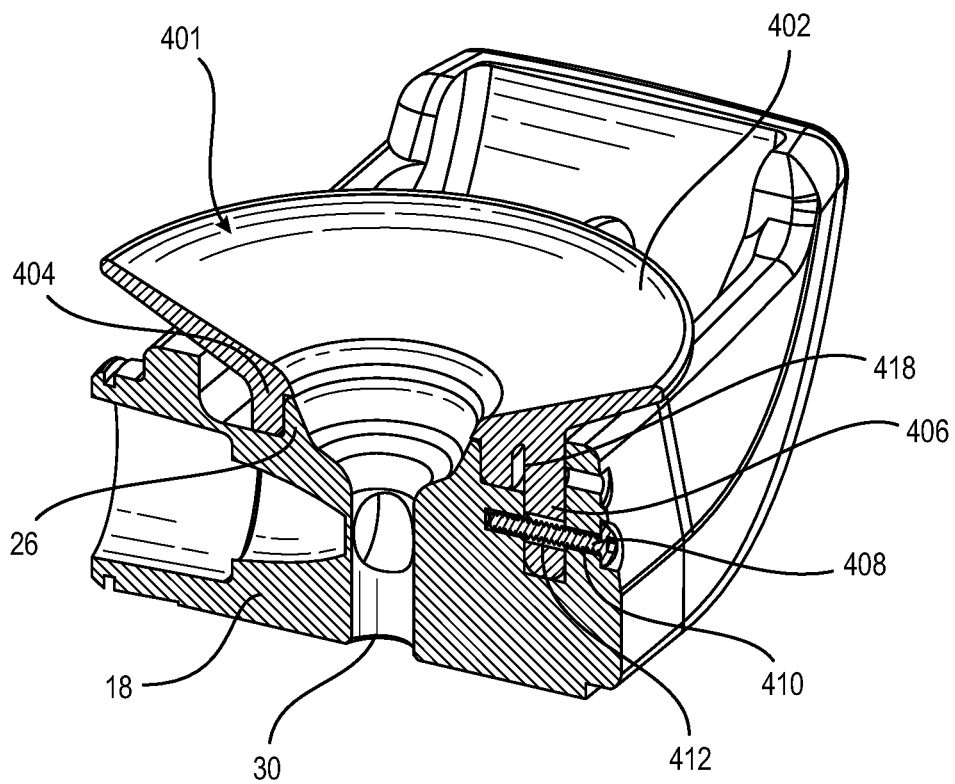
FIG. 7B is a sectional view taken along line VIA-VIA in FIG. 7A.

FIGS. 7A and 7B depict another embodiment of an interchangeable distal end 400 for a prosthetic socket. The interchangeable distal end 400 includes a funnel 401 defining a receiving portion 402 and a stem 404 protruding from the receiving portion 402. The funnel 401 includes a flange 406 extending from the receiving portion 402 and spaced apart a distance 418 from the stem 404. The stem 404 extends about an annular ring 26 of the base 16. The base 16 defines an opening 410 through which a fastener 408 and preferably laterally (generally perpendicularly to the axis of the funnel) extends through an opening 412 defined by the flange 406 and secures to the base 16.

Figure 8:
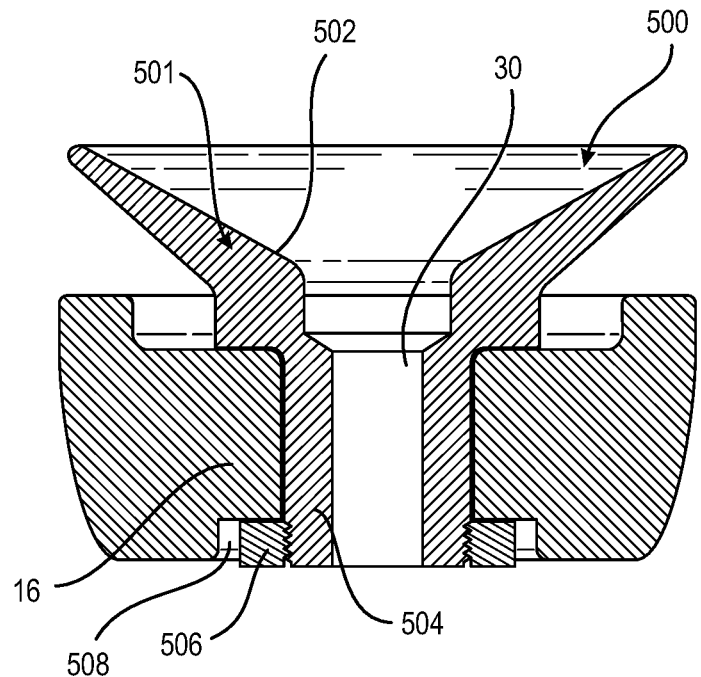
FIG. 8 is a schematic view of another embodiment of a funnel.

FIG. 8 illustrates another interchangeable distal end 500 for a prosthetic socket and includes a funnel 501 defining a receiving portion 502 and a stem 504 protruding from the receiving portion 502. A distal annular ring 506 secures the base 16 within a space 508 formed by the base 16.

Figure 9:
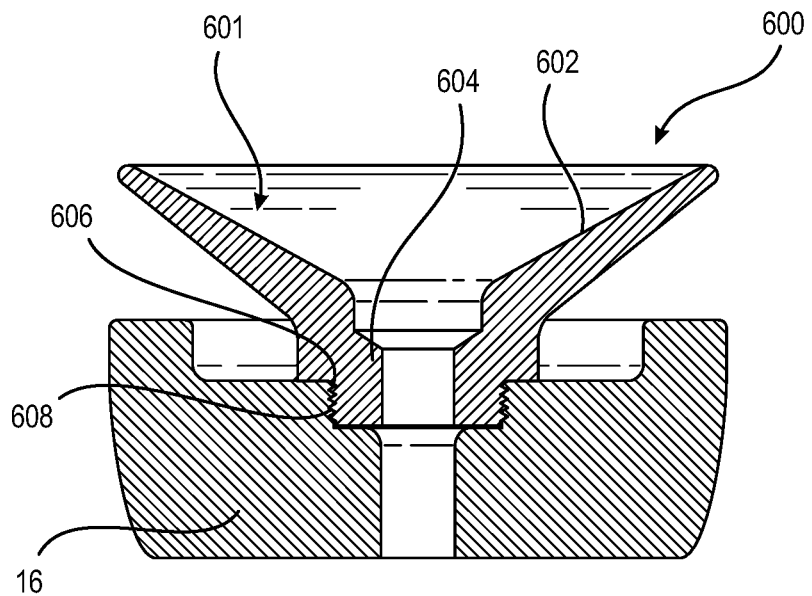
FIG. 9 is a schematic view of another embodiment of a funnel.

FIG. 9 illustrates yet another interchangeable distal end 600 for a prosthetic socket and includes a funnel 601 defining a receiving portion 602 and a stem 604 protruding from the receiving portion 602. The stem 604 forms a threaded section 606 adapted to threadedly engage a threaded portion 608 defines by the base 16.

Figure 10:
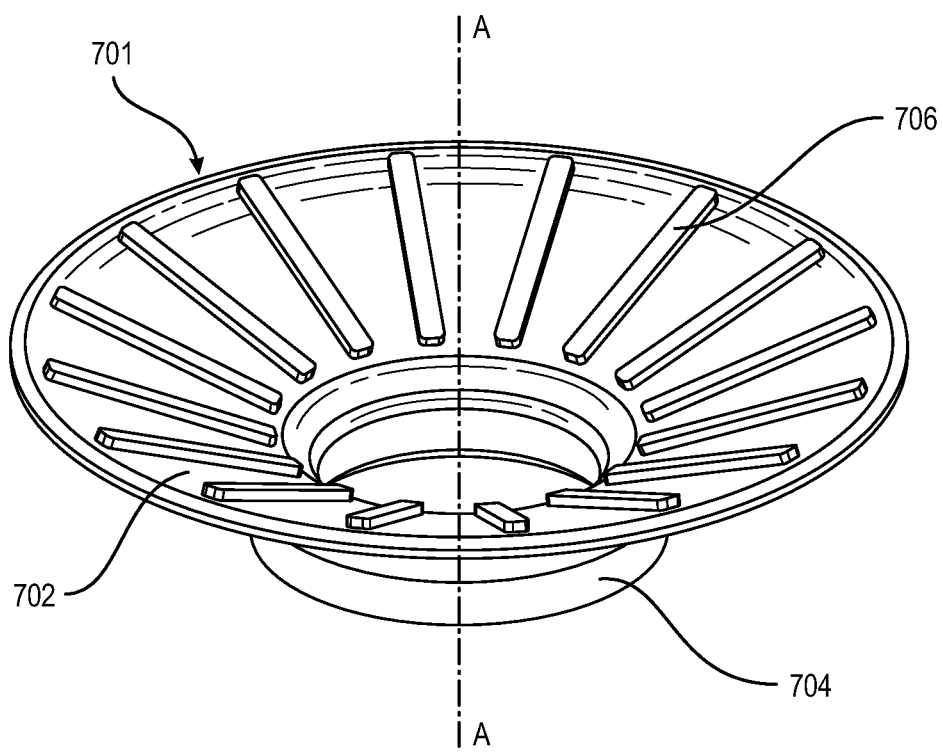
FIG. 10 is a perspective view of another embodiment of a funnel.

FIG. 10 exemplifies a funnel 701 having a receiving portion 702, including a surface 703 along which at least one feature 706 is secured. The at least one feature 706 is formed by a second material having different properties from a first material forming the receiving portion. The at least one feature 706 is formed as a plurality of strips radially extending from an axis A-A of the funnel 701. At least one feature 706 may be formed as any number of different shapes, sizes, and material compositions. The stem 704 may be devoid of such features or possess its own or similar features as the receiving portion 702.

Although this disclosure describes certain exemplary embodiments and examples of an interchangeable distal end, including a funnel, it nevertheless will be understood by those skilled in the art that the present disclosure extends beyond the specifically disclosed prosthetic socket and interchangeable distal end and funnel embodiments to other alternative embodiments and/or users of the disclosure and obvious modifications and equivalents thereof. It is intended that the scope of the present disclosure should not be limited by the particular disclosed embodiments described above, and may be extended to prosthetic devices and supports, and other applications that may employ the features described herein.

The invention claimed is:

1. A prosthetic socket system having an interchangeable distal end, comprising:
   a prosthetic socket defining a base;
   a funnel formed from an elastomeric material and removably attached to the base of a prosthetic socket, the funnel arranged to be positioned in the base;
   wherein the funnel defines a receiving portion having a generally conical shape;
   wherein the funnel forms a stem extending from the receiving portion;
   wherein the funnel forms a central opening extending through the receiving portion and the stem, the central opening defined along a central axis of the funnel;
   wherein the base defines an elongate opening co-axial to the central axis of the central opening;
   wherein the funnel is more flexible than the base;
   wherein the funnel forms at least one mounting portion parallel to the central opening and disposed radially outwardly relative to the stem;
   wherein the stem defines an inner notch formed about an inner periphery of the central opening, the inner notch is adapted to rest along an edge of an inner ring protruding from a proximal side of the base within the central opening, a distal end of the stem surrounding and encircling the inner ring, and is arranged to rest flush against the proximal side of the base;
   wherein the at least one mounting portion is arranged to receive at least one fastener adapted to engage the base and the funnel;
   wherein the at least one mounting portion forms a rib extending generally along a length of the stem;
   wherein the rib defines an aperture and a threaded periphery of the aperture is arranged to engage the at least one fastener.

2. The prosthetic socket system of claim 1, wherein the base defines at least one elongate opening adapted to correspond to the opening of the funnel, and parallel to the central axis of the funnel.

3. The prosthetic socket system of claim 1, wherein the receiving portion defines a concave receiving surface configured and dimensioned to receive a distal end of a residual limb.

4. The prosthetic socket system of claim 1, wherein at least a portion periphery of the receiving portion is generally circular.

5. The prosthetic socket system of claim 1, wherein a periphery of the receiving portion has a circular portion and a linear portion, the linear portion corresponding to a shape of the prosthetic socket.

6. The prosthetic socket system of claim 1, wherein the base defines at least one aperture along a proximal side of the base, the at least one aperture arranged to receive a protrusion extending from a distal side of the funnel.

7. The prosthetic socket system of claim 1, wherein the funnel is formed from an elastomeric material.

8. The prosthetic socket system of claim 1, a receiving portion defines at least one tab generally protruding axially from the receiving portion and adapted to secure to an annular insert formed to attach to the base.

9. A funnel configured and dimensioned for fitting in a base of a prosthetic socket, the funnel comprising:
   a receiving portion having a generally conical shape;
   a stem extending from the receiving portion, the funnel forming a central opening extending through the receiving portion and the stem, the central opening defined along a central axis of the funnel;

at least one mounting portion parallel to the central opening and disposed radially outwardly relative to the stem;

wherein the funnel is formed from an elastomeric material;

wherein the stem defines an inner notch formed about an inner periphery of the central opening, the inner notch adapted to rest along an edge of an inner ring protruding from a proximal side of the base within the central opening, a distal end of the stem adapted to surround and encircle the inner ring, and rest flush against the base;

wherein the at least one mounting portion is arranged to receive at least one fastener adapted to engage the base and the funnel;

wherein the at least one mounting portion forms a rib extending generally along a length of the stem;

wherein the rib defines an aperture and a threaded periphery of the aperture is arranged to engage the at least one fastener.

10. The funnel of claim 9, wherein the receiving portion defines a concave receiving surface configured and dimensioned to receive a distal end of a residual limb.

11. The funnel of claim 9, wherein a periphery of the receiving portion has a circular portion and a linear portion, the linear portion corresponding to a shape of the prosthetic socket.

12. The funnel of claim 9, wherein the base defines at least one elongate opening adapted to correspond to the opening of the funnel, and parallel to the central axis of the funnel.

* * * * *